(12) United States Patent
Berberich et al.

(10) Patent No.: US 9,089,349 B2
(45) Date of Patent: Jul. 28, 2015

(54) DEVICE FOR INTRODUCING MULTIPLE DRILLED CHANNELS IN A BONE

(75) Inventors: Sascha Berberich, Tuttlingen (DE); Daniel Weinmann, Seitingen-Oberflacht (DE)

(73) Assignee: KARL STORZ GMBH & CO. KG (DE)

( * ) Notice: Subject to any disclaimer, the term of this patent is extended or adjusted under 35 U.S.C. 154(b) by 234 days.

(21) Appl. No.: 13/554,365

(22) Filed: Jul. 20, 2012

(65) Prior Publication Data
US 2013/0023891 A1    Jan. 24, 2013

(30) Foreign Application Priority Data
Jul. 22, 2011  (DE) .......................... 10 2011 108 673

(51) Int. Cl.
*A61B 17/17* (2006.01)
(52) U.S. Cl.
CPC ......... *A61B 17/1714* (2013.01); *A61B 17/1764* (2013.01)
(58) Field of Classification Search
CPC ........... A61B 17/1714; A61B 17/1725; A61B 17/1764; A61B 17/17; A61B 17/1721; A61B 17/1739; A61B 17/176
USPC ........................................ 606/80, 96–98, 104
See application file for complete search history.

(56) References Cited

U.S. PATENT DOCUMENTS

| | | | | |
|---|---|---|---|---|
| 4,037,592 A | * | 7/1977 | Kronner | 606/97 |
| 4,383,527 A | * | 5/1983 | Asnis et al. | 606/96 |
| 4,441,492 A | * | 4/1984 | Rydell et al. | 606/67 |
| 4,616,631 A | * | 10/1986 | Takahashi | 600/139 |
| 4,826,280 A | * | 5/1989 | Hiramoto et al. | 385/116 |
| 5,207,753 A | * | 5/1993 | Badrinath | 606/96 |
| 5,324,295 A | * | 6/1994 | Shapiro | 606/86 R |
| 5,349,941 A | * | 9/1994 | Hori | 600/122 |
| 5,681,320 A | * | 10/1997 | McGuire | 606/104 |
| 5,766,221 A | * | 6/1998 | Benderev et al. | 606/232 |
| 6,022,356 A | * | 2/2000 | Noyes et al. | 606/96 |
| 6,086,592 A | * | 7/2000 | Rosenberg et al. | 606/86 R |

(Continued)

FOREIGN PATENT DOCUMENTS

| | | |
|---|---|---|
| DE | 8411993 U1 | 7/1984 |
| DE | 102007057075 A1 | 5/2009 |

(Continued)

OTHER PUBLICATIONS

German Search Report; Application No. DE 10 2011 108 673.4; Issued: Jan. 24, 2012; 6 pages.

*Primary Examiner* — Michael T Schaper
*Assistant Examiner* — Amy Sipp
(74) *Attorney, Agent, or Firm* — Whitmyer IP Group LLC

(57) ABSTRACT

A device for preparing multiple channels in a bone comprises a handle, a single guiding sleeve mounted removable at said handle and an arm projected from said handle. Said single guiding sleeve comprises a central first guiding channel for receiving a first aiming wire, a second guiding channel for receiving a further aiming wire, said channels have parallel axes. At least one cannulation is provided, a central longitudinal axis thereof runs at a distance and parallel to the guiding channels. Said at least one cannulation being arranged offset in a circumferential direction to said second channel. An aiming wire introduced in said second channel can be replaced into a cannulation by pulling off the guiding sleeve turning it about the first aiming wire and reinserting the turned guiding sleeve into said handle.

8 Claims, 9 Drawing Sheets

(56) References Cited

U.S. PATENT DOCUMENTS

| | | | |
|---|---|---|---|
| 6,585,642 B2* | 7/2003 | Christopher | 600/156 |
| 7,674,290 B2* | 3/2010 | McKernan et al. | 623/13.17 |
| 7,762,949 B2* | 7/2010 | Nakao | 600/153 |
| 7,819,879 B2* | 10/2010 | Penenberg | 606/96 |
| 7,927,333 B2* | 4/2011 | Gradl | 606/86 B |
| 8,007,501 B2* | 8/2011 | Kaup et al. | 606/96 |
| 8,109,936 B2* | 2/2012 | Tipirneni | 606/103 |
| 8,579,912 B2* | 11/2013 | Isaza et al. | 606/104 |
| 8,617,168 B2* | 12/2013 | Bourque et al. | 606/87 |
| 2003/0216742 A1* | 11/2003 | Wetzler et al. | 606/96 |
| 2003/0236527 A1* | 12/2003 | Kawakami | 606/96 |
| 2004/0254585 A1* | 12/2004 | Whittaker et al. | 606/104 |
| 2006/0161163 A1 | 7/2006 | Shino | |
| 2007/0213819 A1* | 9/2007 | McKernan et al. | 623/13.11 |
| 2007/0239168 A1* | 10/2007 | Kuenzi et al. | 606/96 |
| 2008/0097453 A1 | 4/2008 | Stone | |
| 2008/0154274 A1* | 6/2008 | Claypool et al. | 606/96 |
| 2009/0069816 A1* | 3/2009 | Sasing et al. | 606/96 |
| 2009/0143784 A1* | 6/2009 | Petersen et al. | 606/96 |
| 2010/0049201 A1* | 2/2010 | Re | 606/89 |
| 2011/0125156 A1* | 5/2011 | Sharkey et al. | 606/92 |
| 2011/0184426 A1* | 7/2011 | Garces Martin et al. | 606/104 |
| 2012/0109136 A1* | 5/2012 | Bourque et al. | 606/87 |
| 2012/0253352 A1* | 10/2012 | Smith | 606/96 |
| 2012/0253353 A1* | 10/2012 | McBride | 606/97 |
| 2013/0012945 A1* | 1/2013 | Chreene et al. | 606/80 |
| 2013/0023891 A1* | 1/2013 | Berberich et al. | 606/98 |
| 2013/0053959 A1* | 2/2013 | Lizardi et al. | 623/13.14 |
| 2014/0288567 A1* | 9/2014 | Kroll | 606/104 |

FOREIGN PATENT DOCUMENTS

| | | |
|---|---|---|
| FR | 2918554 A1 | 1/2009 |
| WO | 2006056754 A1 | 6/2006 |

\* cited by examiner

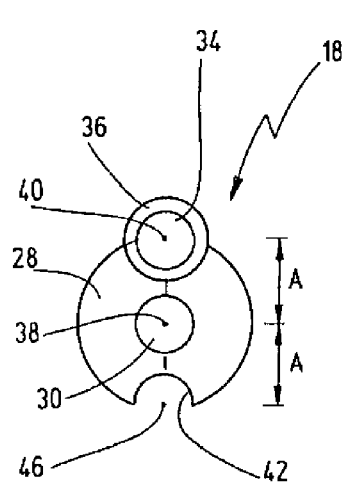
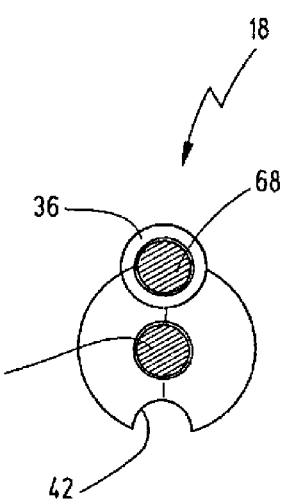
Fig.7  Fig.8  Fig.9
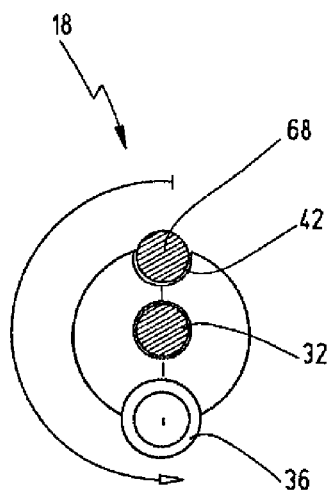
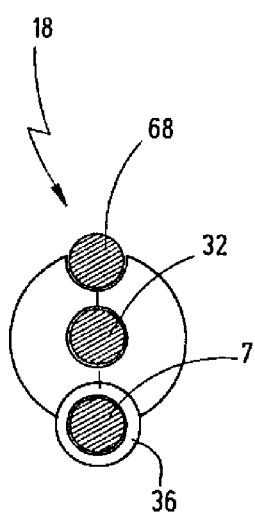
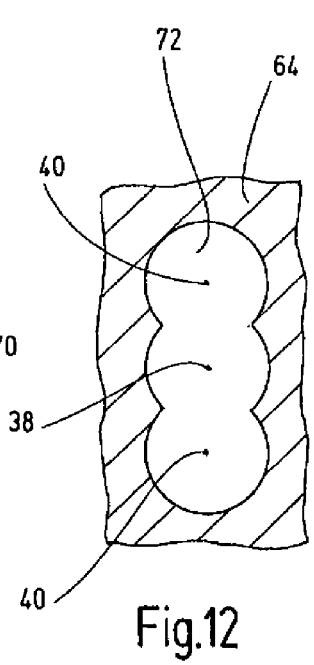
Fig.10  Fig.11  Fig.12

DEVICE FOR INTRODUCING MULTIPLE DRILLED CHANNELS IN A BONE

BACKGROUND OF THE INVENTION

The invention relates to a device for lining up and introducing multiple drilled channels in a bone.

Such a device is known from German Utility Model G 84 11 993.4.

Such devices serve the purpose of preparing drilled channels in a bone, implants being inserted into the drilled channels.

One broad field of use is the reconstruction of cruciate ligaments in the region of the knee. The anterior cruciate ligament extends from the upper plateau (tibial plateau) of the lower leg (tibia) and runs to the inner side of the lower end of the upper leg bone (femur).

In cases of serious injury, the cruciate ligament is completely removed and replaced by a tendon implant.

This tendon implant is often a tendon from the patient itself, for example the semitendinosus ligament, which has proven to be particularly useful for the reconstruction of cruciate ligaments in the knee.

To achieve an alignment of the tendon implant that is as close as possible to the natural alignment, it must be anchored securely in the bone. For this purpose, corresponding drilled holes have to be introduced into the bone.

Since, as mentioned above, the cruciate ligament extends in a quite specific direction from the lower leg bone to the upper leg bone, the drilled holes in these bones into which the tendon implant is to be inserted and anchored should as far as possible likewise extend in this direction.

This allows achievement of the effect that, proceeding from the anchoring site, the tendon implant already extends in the anatomically correct direction from the surface of the bone, for example from the tibial plateau.

For this purpose, exactly aligned drilled holes must be made in the bone.

Since such surgical interventions are carried out arthroscopically and the knee joint represents a complicated and confined joint, the surgeon has relatively little space available for properly lining up and making such drilled holes.

The device mentioned at the beginning has proven to be successful for lining up and introducing drilled channels.

The device of German Utility Model G 84 11 993.4 comprises a handle, which is formed like a bar or grip, and a single guiding sleeve, through which a so-called aiming wire can be pushed. Such aiming wires are relatively stiff, pointed metal wires with a diameter in the range from 2 to 3 mm.

In handling, for example the distal, relatively narrow end of the arm projecting from the device is pushed into the knee joint and placed on the tibial plateau. The distal end of the movable guiding sleeve is usually placed obliquely on an outer side of the lower leg.

If such an oblique drilled hole is to be introduced into the lower leg, the exiting of the drilled hole on the tibial plateau inside the knee joint should take place at a site and at an angle as close as possible to the attachment and alignment of the cruciate ligament to be replaced.

For this purpose, the distal end of the arm which has been pushed into the knee joint has an opening through which the aiming wire that is driven through the bone from the outer side can enter.

After setting the aiming wire, the devices is removed and the guiding sleeve is thereby removed from the aiming wire.

After that, the aiming wire is overdrilled with a hollow drill and this then produces the desired drilled channel in the bone, into which the tendon implant is then inserted and anchored.

With the device of German Utility Model G 84 11 993.4, a surgical technique in which two aiming wires can be set with one and the same device that has only a single guiding sleeve is described. For it, the guiding sleeve has more than one channel for guiding aiming wires.

It is possible to reconstruct the anterior cruciate ligament as anatomically replicating very closely the natural ligament.

In the reconstruction of ligaments, some tendon implants that do not have a circular cross section are used. One reason for this is, for example, that a tendon band of a specific length formed into a U-shaped loop, with legs of the U lying against each other, is used. Such a double strand has in cross section the form of an "8", when provided with an approximate envelope curve an approximately rectangular form.

Transplants with an angular bone block, for example a patella with patellar tendon, or quadricep tendons, are also used.

There is therefore a need for devices with which drilled holes deviating from a circular geometry, in particular polygonal and rectangular drilled holes, can be prepared and produced.

Devices for preparing rectangular drilled holes are known from U.S. 2006/0161163 A, U.S. 2008/0097453 A1 and U.S. Pat. No. 6,022,356 A. Several circular drill holes can be provided close to another or intersecting one another. A dilator inserted into the drill holes shape the resulting opening into a rectangular hole.

SUMMARY OF THE INVENTION

It is therefore the object of the present invention to provide a device capable to accomplish multiple drilled channels lying next to one another, which can then be worked to form corresponding channels deviating from a round geometry.

The object is achieved by a device for preparing multiple channels in a bone comprising a handle, a single guiding sleeve mounted removable at said handle, a distal end of said single guiding sleeve being capable to be placed on a side on a bone, an arm projecting from said handle, a distal end of said arm being capable to be placed on another side of said bone, said single guiding sleeve comprises a central first guiding channel for receiving a first aiming wire, a second guiding channel for receiving a further aiming wire, a central longitudinal axis of said second guiding channel being at a distance from said central longitudinal axis of said first guiding channel and said axes running parallel to one another, at least one cannulation, a central longitudinal axis thereof runs at a distance and parallel to said central axis of said first guiding channel, said at least one cannulation being arranged offset, seen in an circumferential direction extending around said central longitudinal axis of said first guiding channel, at an circumferential angle to said second guiding channel, and a further aiming wire introduced into said second guiding channel can be transferred to said at least one cannulation by pulling off said guiding sleeve from said handle, turning said guiding sleeve about said first aiming wire received in said central first guiding channel up to an alignment of said further aiming wire with said at least one cannulation and reinserting said turned guiding sleeve into said handle.

These measures have numerous advantages.

Providing the second guiding channel, which runs at a distance A from and parallel to the central longitudinal axis of the first guiding channel, creates the basic precondition for setting two aiming wires lying next to each other and running parallel to each other. In this case, the distance A may be chosen such that, after overdrilling the aiming wires, the two resultant circular drilled holes overlap, so that this alone in principle allows a channel that already has approximately a rectangular circumferential profile to be accomplished.

Providing the cannulation at an outer side of the guiding sleeve, which, as far as its central longitudinal axis is concerned, likewise runs at the distance A from the central longitudinal axis of the central channel and likewise extends parallel to this axis, opens up the possibility of performing the following procedures.

After setting the first two aiming wires, the guiding sleeve may be pulled off from the handle to an extent that it is still but only located on the central, correspondingly longer, first aiming wire, but no longer holds the second aiming wire. Consequently, the second aiming wire has left the second guiding channel. Then, the guiding sleeve may be turned by an appropriate angle about the first aiming wire until the second aiming wire is in line with the cannulation in the outer side on the guiding sleeve. By advancing the guiding sleeve in the distal direction i.e. reinserting it into the handle, the second, or last-set, aiming wire is pushed into the cannulation. Since in this state the second guiding channel is no longer occupied, a third aiming wire can be pushed through it and introduced into the bone.

Depending on the number of these cannulations and the circumferential angular orientation, further aiming wires in addition to the two aiming wires that have been set through the first and second guiding channels can then also be set. If only one such cannulation is present, and if for example it lies diametrically opposite the second guiding channel, three aiming wires running parallel to one another can be set. After overdrilling the three set aiming wires with appropriate hollow drills, then a drilled hole which, seen in cross section, is relatively elongated and approximately rectangular is obtained.

If the cannulation is not offset in terms of the circumferential angle by 180° but by a different angle, correspondingly angled-away drilled hole profiles are obtained.

If there are multiple circumferentially angularly offset outer cannulations, other geometrical formations can also be achieved, such as "T"-shaped or "†"-shaped drilled holes. For the surgeon, handling can be carried out easily and safely, since the same course of action is always followed.

This involves aiming and setting the device in the known and accustomed way, as when only a single aiming wire is intended to accomplish the provision of only a single circular drilled hole. The provision of the second guiding channel allows the second aiming wire firstly to be set directly adjacent and parallel to the first aiming wire. Then, the removable guiding sleeve is pulled off to the extent that the second aiming wire is exposed, but the guiding sleeve is still pushed on the first aiming wire. By turning the guiding sleeve by the desired angle about the first aiming wire, a third aiming wire, or possibly multiple further aiming wires, can be set as desired. The aiming wires respectively set beforehand through the second drilled channel are then placed in the open cannulation or cannulations.

After that, the device can be removed and the aiming wires that are set and fixed in the bone can be overdrilled with appropriate hollow drills, in order then to produce the desired drilled hole with the desired cross-sectional profile in the bone.

In a refinement of the invention, there is a single cannulation, which is arranged angularly offset in relation to the second guiding channel by an angle of up to 180°.

As mentioned above, this measure has the advantage that three aiming wires can be set directly adjacently, to be precise between a linear alignment, as seen over a joining line of the central axes of the aiming wires, and an angled-away alignment.

In a further refinement of the invention, the single cannulation is angularly offset exactly by 180°.

This measure has the advantage that an exactly straight-aligned drilled hole with a rectangular cross section can be accomplished by this refinement.

In a further refinement of the invention, there are three cannulations, which are respectively arranged angularly offset in relation to the second guiding channel by 90°.

This measure has the advantage that it allows multiple different cross sections of drilled holes to be achieved.

For one thing, as mentioned above, if only the 180° angularly offset cannulation is occupied, it is possible to accomplish the straight-extending cross-sectionally rectangular opening.

If a cannulation which is angularly offset only by 90° is occupied, a correspondingly angled away drilled hole is achieved.

If two of these cannulations are occupied, an approximately "T"-shaped cross-sectional structure is achieved.

If all three cannulations are occupied, a "symmetrically cruciform" profile can be achieved.

In a further refinement of the invention, the guiding sleeve has an approximately bar-shaped body, in which the first guiding channel is centrally cut out, and the second guiding channel is set on the body.

This measure has the advantage that the two guiding channels can be produced very simply in terms of production technology and the surgeon is provided right away with an orientation feature in the form of the outer, set, second guiding channel, from which he knows in which position and orientation the second guiding channel is in relation to the first guiding channel. Thus, the guiding sleeve may consist of a bar-shaped body which centrally has a bore that represents the first circumferentially closed guiding channel. Joined or placed onto this body there may then be the second guiding channel in the form of a guiding tube. For this purpose, this guiding tube may be placed onto the outer side or inserted into a correspondingly cut-in depression and fastened therein, this being determined in part by the respective dimensions, in particular the distance A.

In a further refinement of the invention, the at least one cannulation is formed as a longitudinal laterally open groove along the body of the guiding sleeve.

This measure has the advantage that this groove can be easily produced exactly to size and in the correct position by milling out the body. This also facilitates the handling to the extent that, after setting the first two aiming wires and after pulling off the guiding sleeve and turning it about the longer central aiming wire, the guiding sleeve merely has to be advanced linearly again, the second aiming wire then entering this longitudinal groove. Due to the fact that the groove is laterally open to the outside, some minor misalignments of the second or further aiming wire which has to be transferred into the groove can be tolerated.

In a further refinement of the invention, cut out in the handle is an opening, which is adapted to the outer contour of the guiding sleeve such that the guiding sleeve can only be pushed into the opening in certain alignments only.

This measure also facilitates the handling to the extent that, after pulling off and turning the guiding sleeve, the handling person can only push said sleeve back into the opening in specific rotational positions, that is to say the rotational positions that correspond to the desired rotational angle or angles.

In a further refinement of the invention, at the distal end of the arm there is an opening through which an aiming wire pushed through the first guiding channel can be passed.

This measure, which is known per se, has the considerable advantage that the device is held on the first aiming wire at two opposite positions of the bone, to be specific on one side by way of the opening through which the aiming wire reaches through the distal end of the arm and on the opposite side also through the guiding sleeve resting on the first aiming wire.

In a further refinement of the invention, markings are provided at the distal end of the arm, adjacent to the opening, representing target points of the further aiming wires, which run through the second guiding channel and the at least one open cannulation.

This measure has the advantage that, after forcing through the second and further aiming wires, the surgeon can check on the basis of the markings whether these aiming wires are set exactly.

In a further refinement of the invention, the first guiding channel is formed as a circumferentially closed guiding channel.

This measure has the advantage that, as a result, the pulled-off guiding sleeve can be turned in an exactly guided manner about the set first aiming wire, without a radial displacement or positional change of the guiding sleeve being possible.

It goes without saying that the features mentioned above and those still to be explained below can be used not only in the respectively specified combinations but also in other combinations or on their own without departing from the scope of the present invention.

BRIEF DESCRIPTION OF THE DRAWINGS

The invention is described and explained in more detail below on the basis of several selected exemplary embodiments in conjunction with the accompanying drawings, in which:

FIG. 7 shows a cross section through the guiding sleeve, approximately half-way along, of the exploded representation of FIG. 1, FIG. 8 shows a corresponding cross section in the state of FIG. 2, FIG. 9 shows a corresponding cross section in the structural state represented in FIG. 3, FIG. 10 shows a cross section of the structural state of FIG. 5, after the guiding sleeve has been pushed in again, FIG. 11 shows a corresponding cross section of the structural state of FIG. 6, FIG. 12 shows a sectional representation through a bone into which the three aiming wires have been set, after overdrilling by hollow drills.

DETAILED DESCRIPTION OF PREFERRED EMBODIMENTS

Figure 1:
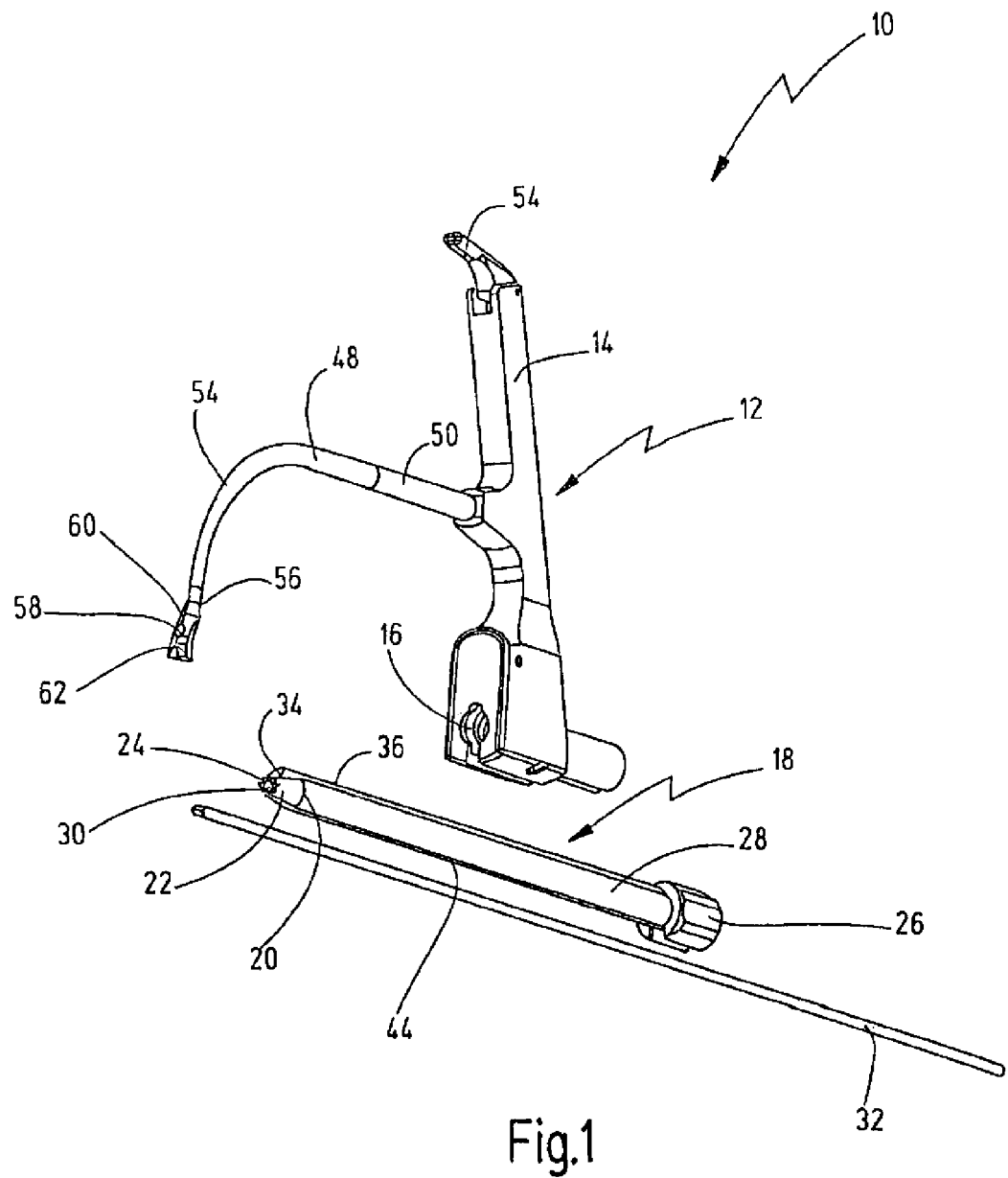
FIG. 1 shows an exploded view of a first exemplary embodiment of a device according to the invention.

A first exemplary embodiment of a device according to the invention that is represented in FIGS. 1 to 11 is denoted overall by the reference numeral 10.

The device 10 has a handle 12, which has an approximately bar-shaped grip 14.

Provided at one end of the handle 12 is an opening 16, which serves for removably receiving a guiding sleeve 18.

As can be seen in particular from the sectional representation of FIG. 7, the guiding sleeve 18 is formed approximately in the form of a tube 20, the distal end 22 of which is provided with a serrated rim 24 (FIG. 1). At the opposite end, the guiding sleeve 18 is provided with a rotatable clamping sleeve 26.

In the actual body 28 of the guiding sleeve 18 there is a first, central continuous guiding channel 30, which in the present case is formed as a central bore passing through the body 28. The clear inside diameter of the first guiding channel 30 is such that a first aiming wire 32, as represented in FIG. 1, can be pushed snugly through it. The aiming wire 32 has an outside diameter of 2.4 mm. Laterally offset in relation to the first guiding channel 30 there is a second guiding channel 34, which represents the inner lumen of a guiding tube 36. The guiding tube 36 is fitted in a recess (not designated any more specifically here) on the outer side of the body 28 of the guiding sleeve 18 and fastened therein, for example adhesively bonded or welded or soldered.

It is evident from the sectional representation of FIG. 7 that the central longitudinal axis 38 of the first guiding channel 30 runs parallel to and at a distance A from the central longitudinal axis 40 of the second guiding channel 34. FIG. 1 and the sectional representation of FIG. 7 also reveal that on the outer side of the body 28 there is also a cannulation 42, to be precise in the form of a cross-sectionally semicircular longitudinal groove 44. The cannulation 42 is open to an outside laterally to the central longitudinal axis 38.

It can again be seen from the sectional representation of FIG. 7 that a virtual central longitudinal axis 46 of the longitudinal groove 44 likewise lies at a distance A from the central longitudinal axis 38 of the first guiding channel 30.

Furthermore, the central longitudinal axis 46 or the longitudinal groove 44 lies exactly diametrically opposite the second guiding channel 34. In other words, the cannulation 42 or the central longitudinal axis 46 thereof is arranged offset in relation to the second guiding channel 34 or the central longitudinal axis 40 thereof in terms of the circumferential angle by 180°.

Figure 2:
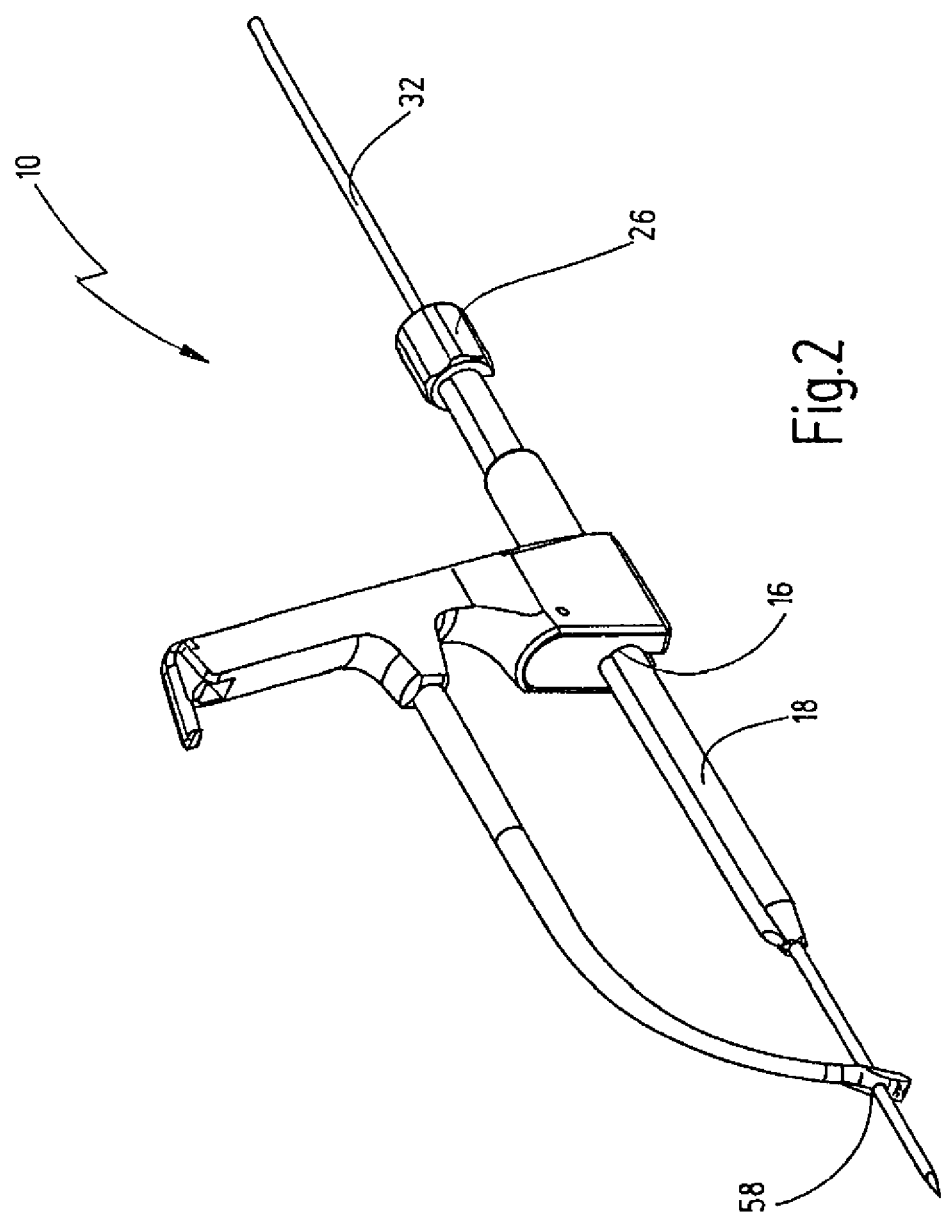
FIG. 2 shows the device of FIG. 1 in the assembled state, it being shown that a first aiming wire has already been pushed through the guiding sleeve.

Returning to the representation of FIGS. 1 and 2, it is evident that an arm 48, which is held in a mounting 50, projects from the handle 12 at a distance from and approximately parallel to the guiding sleeve 18.

A clamping lever 54 keeps the arm 48 in the position represented; pressing of the clamping lever 54 allows the removal of the arm 48, and it can correspondingly be cleaned or replaced by a new or differently formed arm.

The arm 48 has distally a bent region 54, the distal end 56 of which has an opening 58. The position of the opening 58 is such that it is in line with the first guiding channel 30 when the guiding sleeve 18 has been pushed into the opening 16 on the handle 12, as is evident in particular from FIG. 2.

This means that, if a first aiming wire 32 is pushed through the guiding sleeve 18 from proximally, that is a say in the region of the clamping sleeve 26, it meets the opening 58 and can pass through it.

Figure 13:
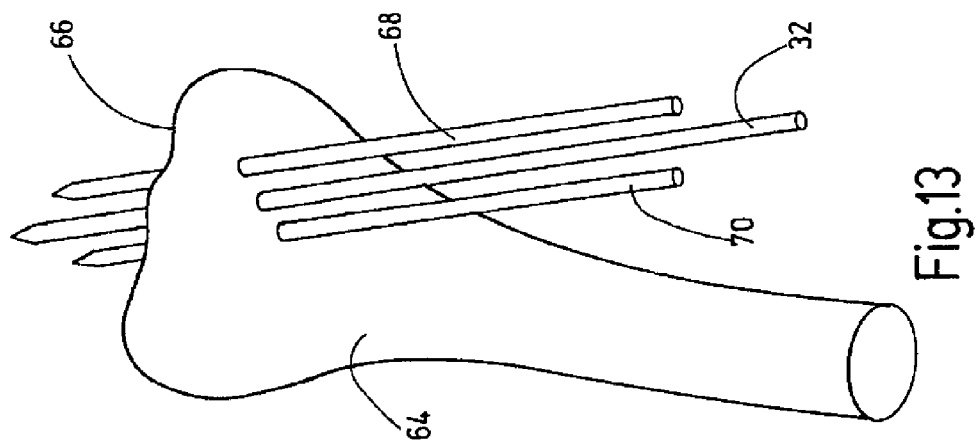
FIG. 13 shows a perspective representation of a lower leg bone into which the three aiming wires have been set, that is to say after pulling off of the device from the structural state of FIG. 6.

As described and explained in more detail in particular by DE 10 2007 057 075.0 A1, the device 10 is set laterally inclined onto the outer side of a bone, for example onto the lower leg bone 64 represented in FIG. 13. The serrated rim 24 thereby facilitates the setting and holding of the guiding sleeve 18 at this site of the bone 64 or on the skin covering this bone.

The distal end 56 of the bent arm 48 is thereby introduced into the opened knee joint and positioned on the tibial plateau 60 such that a first aiming wire 32 pushed through the bone 64, as is evident in FIG. 13, passes through the tibial plateau 60 and is passed through the opening 58.

For the sake of overall clarity, the bone is not represented in FIG. 2, since this first working step is known per se from DE 10 2007 057 075.0 A1 which is incorporated by reference.

The handling and setting of the further aiming wires will now be described and explained in more detail on the basis of the sequence of images of FIG. 3 to FIG. 6 and the sectional representations of FIG. 8 to FIG. 11.

Figure 3:
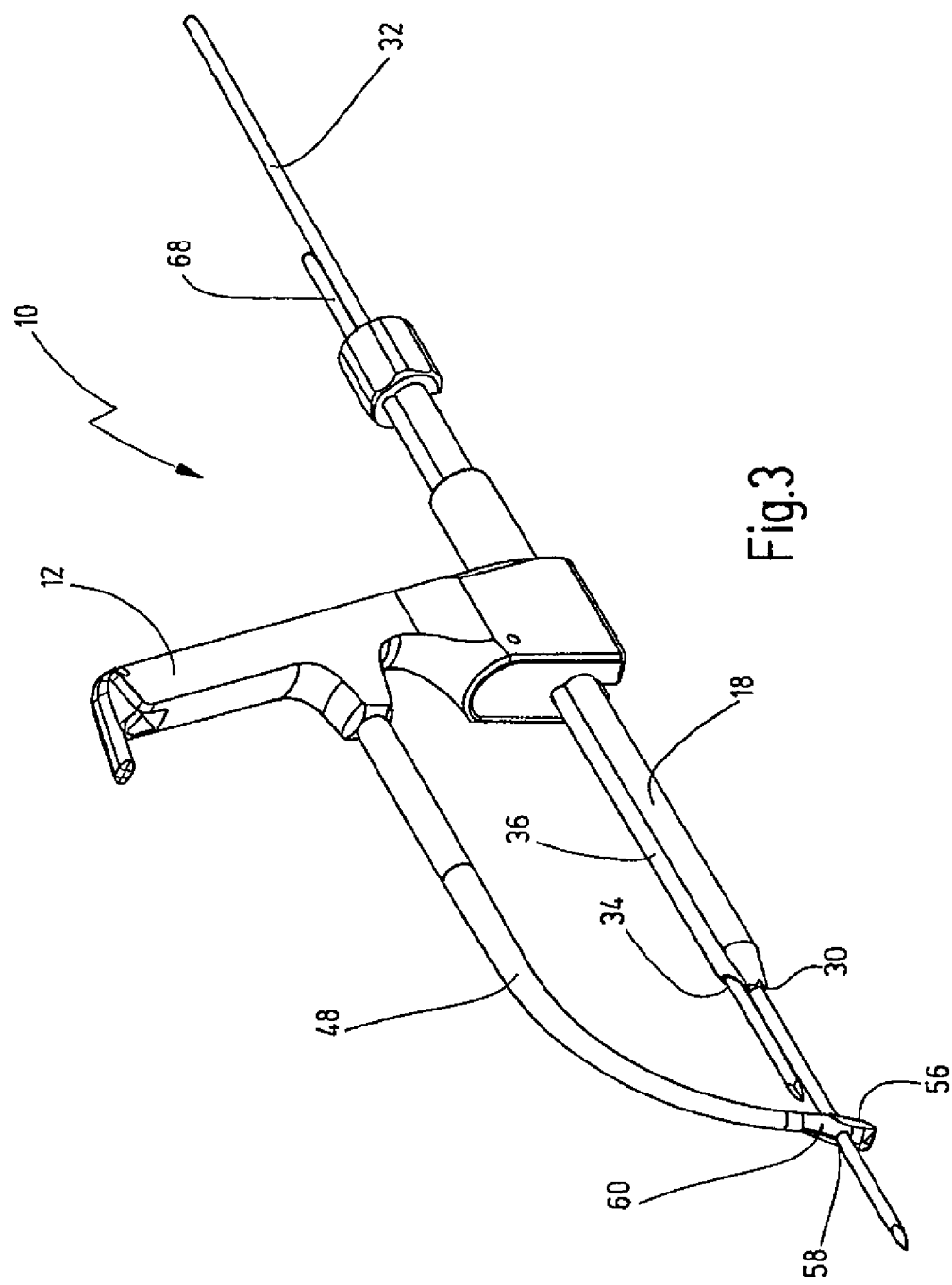
FIG. 3 shows a representation corresponding to FIG. 2, it being shown that a second aiming wire has been pushed through the second guiding channel.

After setting of the first aiming wire 32, as represented in FIG. 2, a further or second aiming wire 68 is set through the second guiding channel 34, as is evident in FIG. 3 or FIG. 9.

It is evident that the first aiming wire 32 is significantly longer than the further, second aiming wire 68. In its maximum advanced position, the distal tip (not represented any more specifically here) of the second aiming wire 68 reaches up to the marking 60 at the distal end 56 of the curved arm 48. Once it has reached this point, that is an indication to the surgeon that the second, further aiming wire 68 has been set in the correct position and in the correct line.

Figure 4:
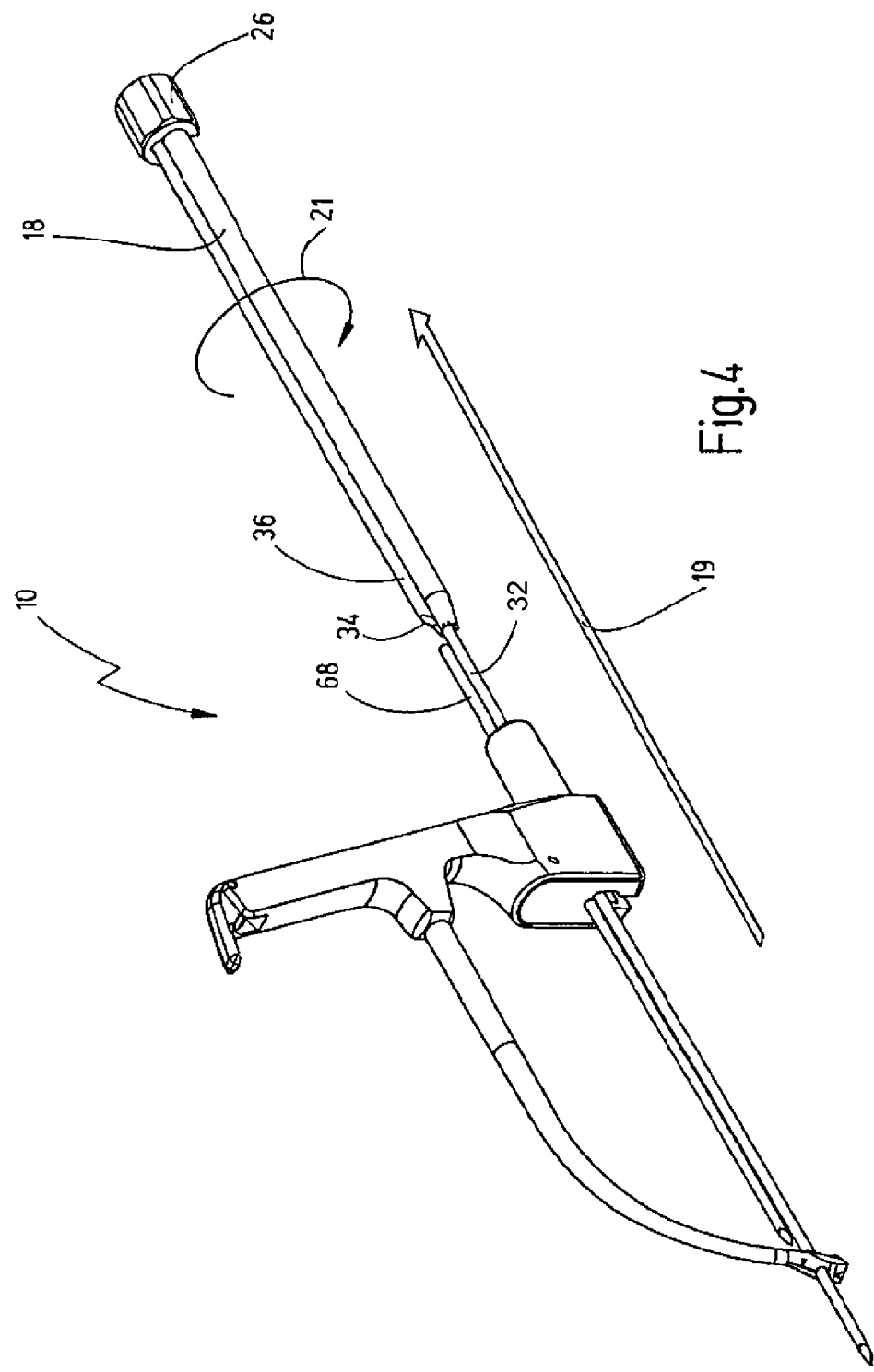
FIG. 4 shows a representation of the device in a state during handling in which the guiding sleeve has been pulled from the second aiming wire but is still located on the first, longer aiming wire.

Then the clamping sleeve 26 is turned, so that the guiding sleeve 18 can be pulled off in the proximal direction (see arrow 19) until the second, further aiming wire 68 has left the second guiding channel 34, this structural state being represented in FIG. 4. The length of the pulling-off distance is intended to be represented by the arrow 19.

Figure 5:
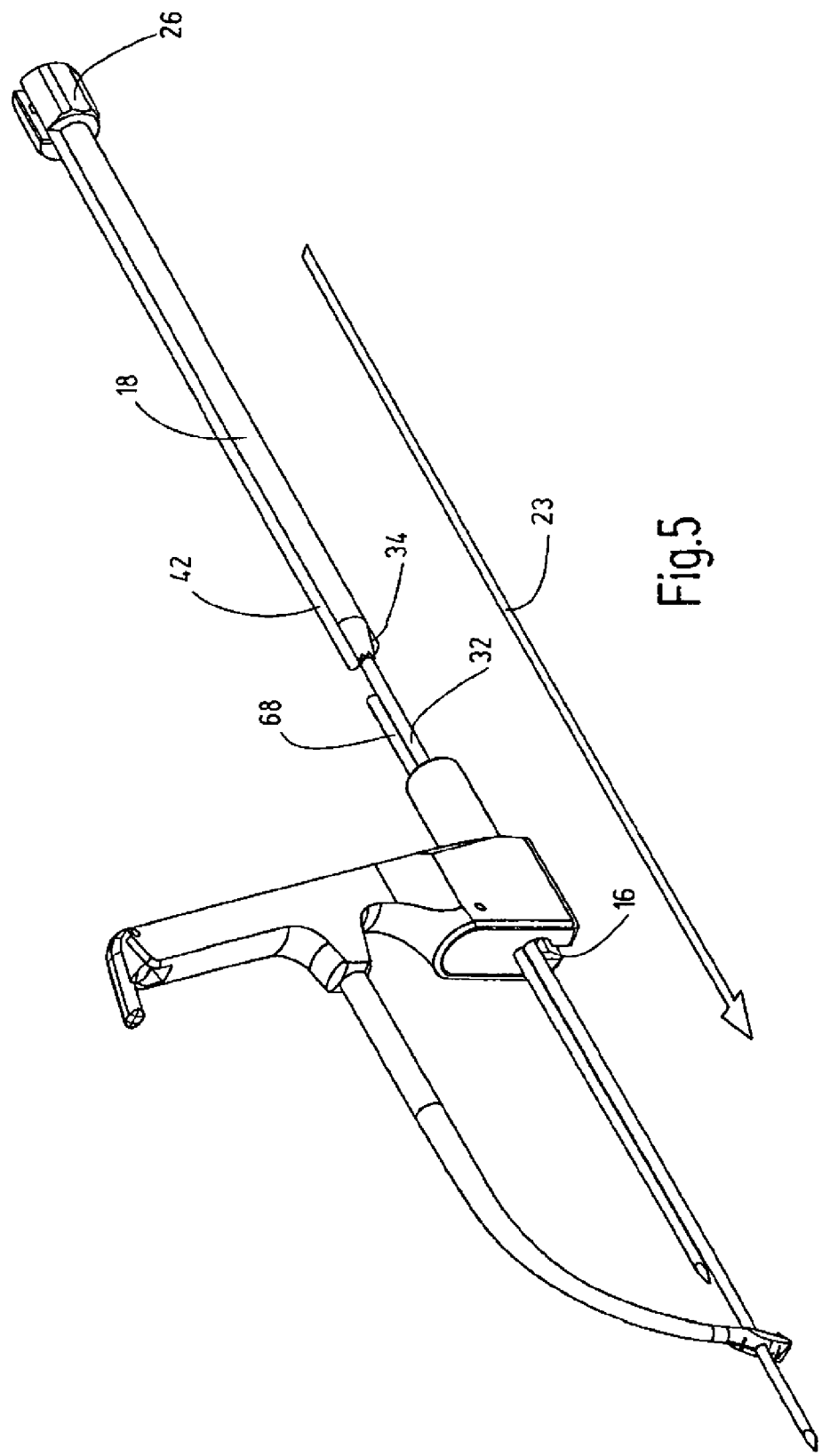
FIG. 5 shows a representation corresponding to FIG. 4, after the guiding sleeve has been turned about the first aiming wire by 180°.

It is then possible to turn the guiding sleeve 18 about the first aiming wire 32, as represented in FIG. 4 by the arrow 21. The turning is carried out through 180°, so that then the cannulation 42 on the outer side of the guiding sleeve 18 lies in an alignment in which the second aiming wire 68 can enter the cannulation 42 during advancement of the guiding sleeve 18. This situation is represented in FIG. 5.

If the guiding sleeve 18 is then displaced in the distal direction in a way corresponding to the arrow 32, the aiming wire 68 enters the cannulation 42 (see FIG. 10). Subsequently, the guiding sleeve 18 is pushed through the opening 16, this opening being designed such that the guiding sleeve 18 can be pushed through either in this position or in the position turned by 180°. After fixing by the clamping sleeve 26, a third aiming wire 70 is then pushed through the second guiding channel 34 or the guiding tube 36, lying on the underside in the representation of FIG. 5.

Figure 6:
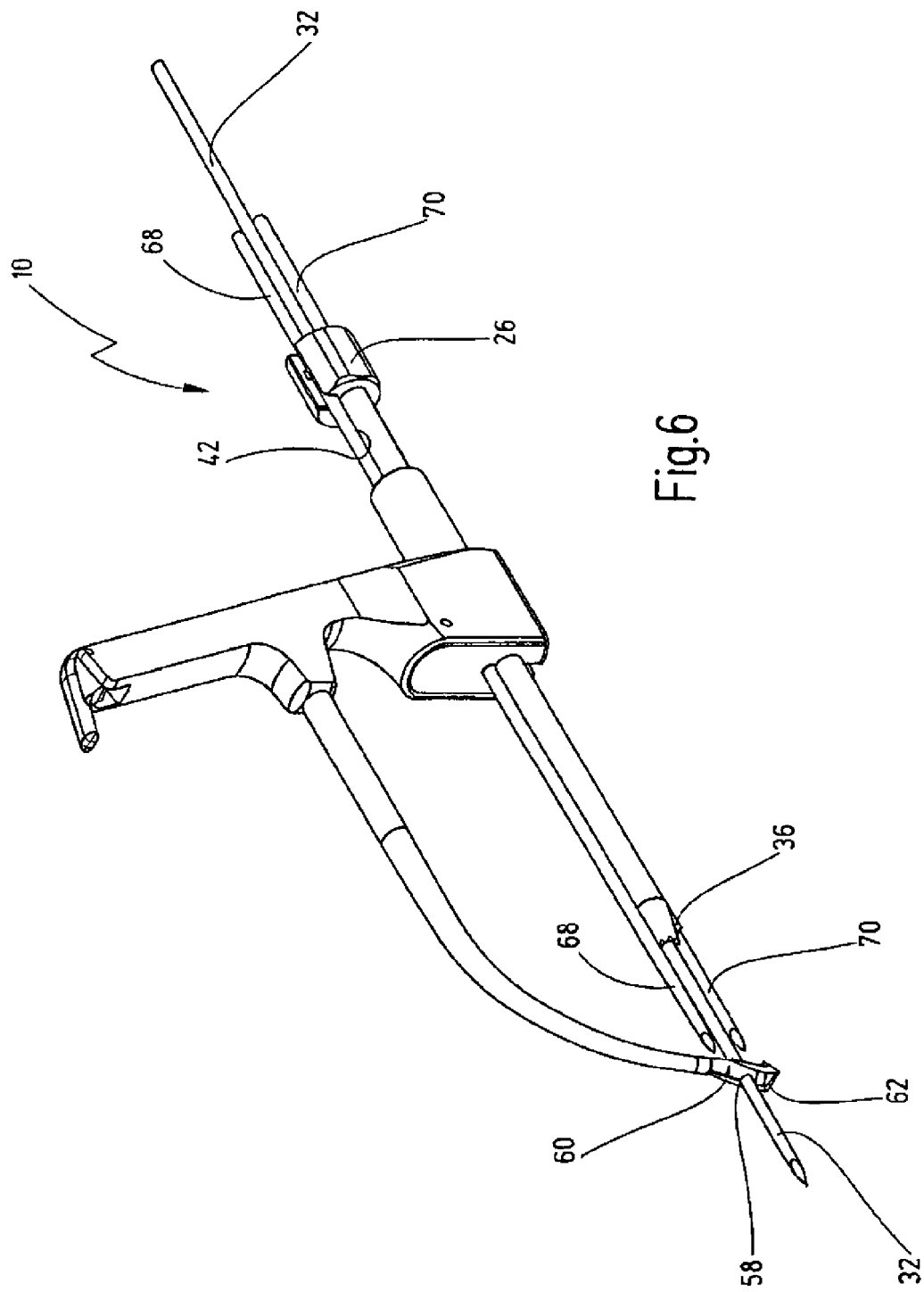
FIG. 6 shows a state after the guiding sleeve has been pushed in again from the position of FIG. 5, the second aiming wire has entered the first cannulation and a third aiming wire has already been set through the second guiding channel.

This situation is represented in FIG. 6 and in FIG. 11.

The third aiming wire 70 can also be advanced until it reaches the corresponding marking 62 at the distal end 56 of the arm 48, so that again the surgeon can check whether this third aiming wire 70 also protrudes from the tibial plateau 66 at the correct site.

Subsequently, the guiding sleeve 18 is pulled off and the arm 48 is detached from the handle 12, so that the entire device 10 is removed from the three set aiming wires 32, 68 and 70.

This situation is represented in FIG. 13, that is to say the three aiming wires 32, 68 and 70 have been pushed through into the lower leg bone 64 from "below" by means of the device 10 such that they all three stand up from the tibial plateau 66 aligned parallel to one another.

The distance A between the three central longitudinal axes of the three aiming wires 32, 68 and 70 is chosen such that they can be overdrilled with a 4.5 mm drill. This initially involves overdrilling the two outer aiming wires 68 and 70 and subsequently likewise overdrilling the middle aiming wire 32.

Figure 14:
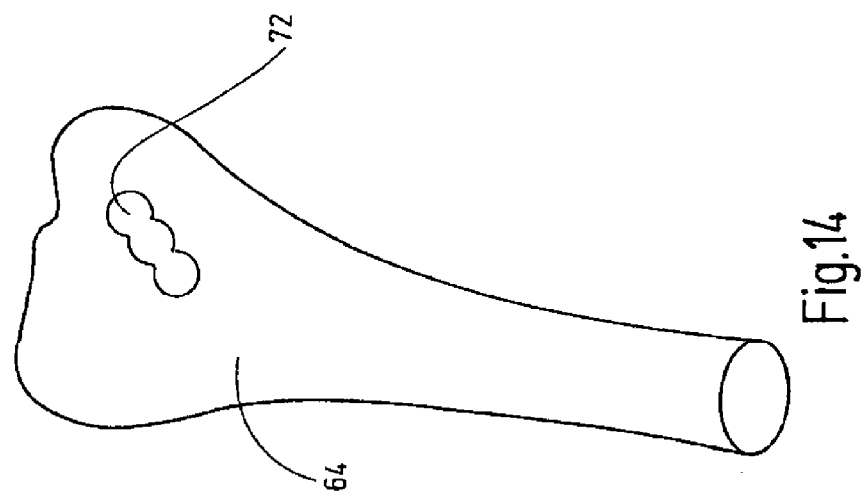
FIG. 14 shows a state of the bone corresponding to FIG. 12, after overdrilling and pulling off of the three aiming wires.

This then results in a drilled hole 72, as represented in FIGS. 12 and 14.

Figure 15:
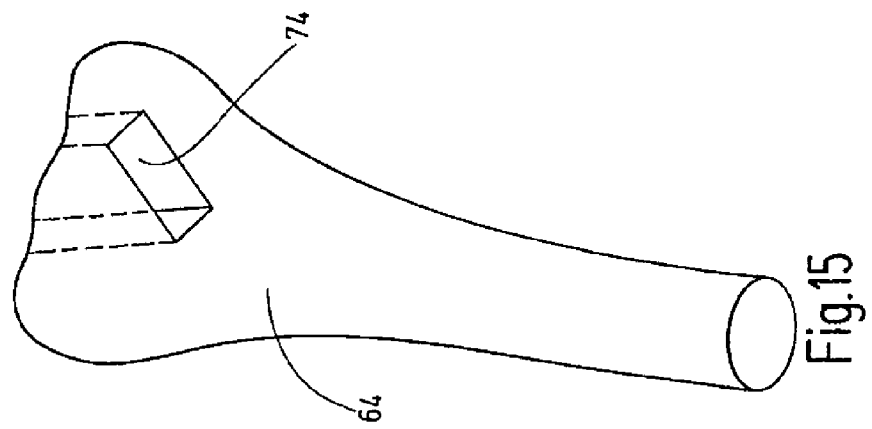
FIG. 15 shows the bone of FIG. 14 after a possible reworking by a bone spatula to form an exactly rectangular drilled-hole cross section.

If an exactly rectangular channel 74, as represented in FIG. 15, is to be achieved, a correspondingly rectangular dilator may be pushed into the drilled hole 72, in order to detach the protruding regions of bone remaining in the region of intersection.

In the reconstruction of an anterior cruciate ligament, a rectangular tendon transplant, for example, with the correct fit and form can then be inserted into the channel 74 and anchored.

In FIGS. 16 to 21, a second exemplary embodiment of a device according to the invention is represented, the difference merely being that the guiding sleeve 78, and correspondingly the opening into which the latter can be pushed into the handle 12, are formed differently.

Figure 16:
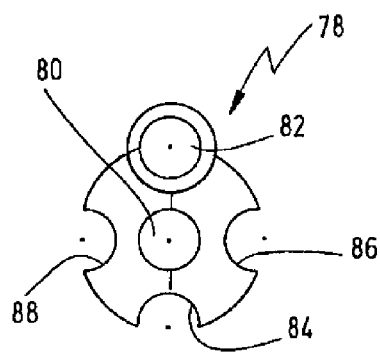
FIG. 16 shows a cross-sectional representation comparable to FIG. 7 of a second exemplary embodiment of a guiding sleeve, with three open cannulations on the outer side.

It can be seen from the sectional representation of FIG. 16, which corresponds to the sectional representation of FIG. 7, that here too there is a central, first guiding channel 80. At the previously described distance A and running parallel to it there is a second guiding channel 82. Here, too, in the outer side of the guiding sleeve 78 there is a first cannulation 84, the central longitudinal axis of which again runs parallel to and at the same distance A from the central longitudinal axis of the first guiding channel 80, as described above in conjunction with the first exemplary embodiment.

As a departure from the first exemplary embodiment, in the case of the second exemplary embodiment a second and a third cannulation 86 and 88 are also cut out on the outer side of the guiding sleeve 78. These cannulations again take the form of longitudinally running and laterally open grooves with an approximately semicircular cross section and the central longitudinal axes of which are again at the distance A from the central longitudinal axis of the first guiding channel 80.

As described above, with the second exemplary embodiment three aiming wires running parallel to one another and aligned in a row can be set.

In addition, however, it is also possible now to achieve other geometries on resultant drilled holes.

Figure 17:
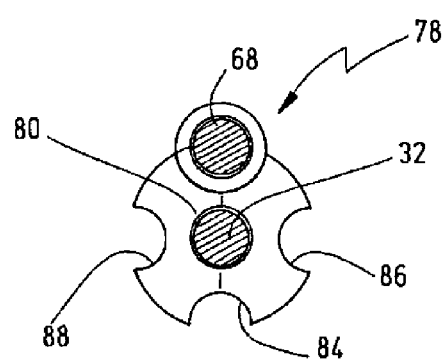
FIG. 17 shows a structural state corresponding to FIG. 9.

FIG. 17 corresponds to a structural state such as that described in FIG. 9, that is the state after the first two aiming wires 32 and 68 have been set.

Figure 18:
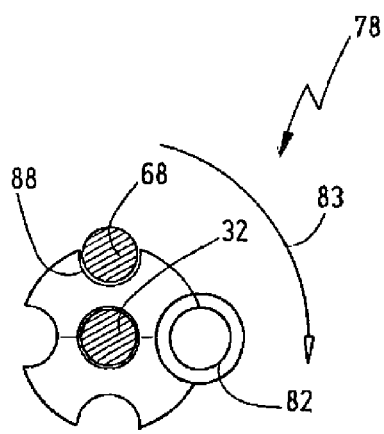
FIG. 18 shows a structural state comparable to that of FIG. 10, although here the guiding sleeve has been turned only by 90°.

As is evident from the transition from FIG. 17 to FIG. 18, after pulling off of the guiding sleeve 78 from the second aiming wire 68, the latter is turned only by 90°, as indicated by an arrow 83. Subsequently, the guiding sleeve 78 is pushed in again axially.

Figure 19:
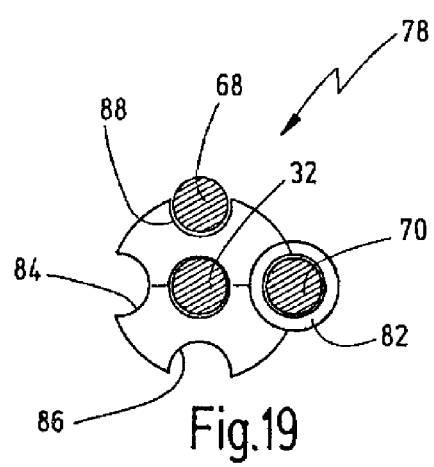
FIG. 19 shows a structural state comparable to FIG. 11, with three set aiming wires.

As a result, the second aiming wire 68 then enters the fourth cannulation 88, angularly offset anticlockwise by 90°. A third aiming wire 70 can then be pushed in through the second guiding channel 82, so that the alignment of the three aiming wires 32, 68, 70 at the corners of a triangle resulting from FIG. 19 is obtained.

Figure 20:
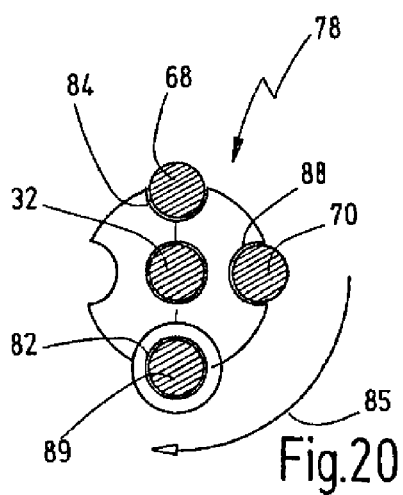
FIG. 20 shows a structural state after a further turning by 90°, with four set aiming wires.

Renewed detachment and pulling off of the guiding sleeve 78 from the third aiming wire 70 allows the guiding sleeve 78 to be turned once again by 90°, as represented in FIG. 20 by an arrow 85.

The third aiming wire 70 has then entered the third cannulation 88; the second aiming wire 68 lies in the first cannulation 84. A fourth aiming wire 89 can then be set in the second guiding channel 82, which has become free again.

Figure 21:
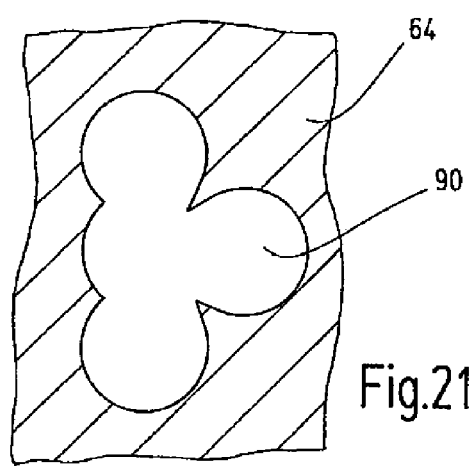
FIG. 21 shows a representation comparable to the representation of FIG. 12, with a drilled hole after overdrilling of the four aiming wires of FIG. 20 to achieve an opening with a "T" profile.

After removal of the device and overdrilling of the four aiming wires 32, 68, 70 and 89, a drilled hole 90 with an approximately "T"-shaped profile, as represented in FIG. 21, then results in the bone 64.

What is claimed is:

1. A device for preparing multiple channels in a bone comprising,
    a handle,
    a single guiding sleeve mounted removably at said handle,
        a distal end of said single guiding sleeve being capable of being placed on a side on the bone,
    an arm projecting from said handle, a distal end of said arm being capable of being placed on another side of said bone,
    said single guiding sleeve comprising
        a central first guiding channel for receiving a first aiming wire, wherein said central first guiding channel is circumferentially closed within the guiding sleeve,
        a second guiding channel, wherein said second guiding channel is circumferentially closed within the guiding sleeve, a central longitudinal axis of said second guiding channel being at a distance A from a central longitudinal axis of said first guiding channel, said axes running parallel to one another, and
        at least one cannulation, a central longitudinal axis thereof runs at said distance A and parallel to said central axis of said first guiding channel, said at least one cannulation being arranged offset, seen in a circumferential direction extending around said central longitudinal axis of said first guiding channel, at a circumferential angle to said second guiding channel, wherein said at least one cannulation is shaped as a longitudinally extending and laterally open groove on a body of said guiding sleeve, said laterally open groove being open along an entire length of said body of said guide sleeve,
    wherein the device further comprises a further aiming wire introduced into said second guiding channel can be transferred to said at least one cannulation by pulling off said guiding sleeve from said handle, turning said guiding sleeve about said first aiming wire received in said central first guiding channel to achieve alignment of said further aiming wire with said at least one cannulation and reinserting said turned guiding sleeve into said handle,
    wherein said laterally open groove allows tolerating misalignments of said further aiming wire when transferring said further aiming wire from said second guiding channel to said laterally open groove.

2. The device of claim 1, wherein the at least one cannulation is a single cannulation, which is arranged angularly offset in relation to said second guiding channel by an angle of up to 180°.

3. The device of claim 1, wherein the at least one cannulation is a single cannulation, which is arranged angularly offset in relation to said second guiding channel by 180°.

4. The device of claim 1, wherein the at least one cannulation comprises three cannulations, and wherein two cannulations are arranged angularly offset in relation to said second guiding channel in each case by 90°, and the other cannulation is offset by 180° in relation to said second guiding channel.

5. The device of claim 1, wherein said guiding sleeve has an approximately elongated cylinder-shaped body, said first guiding channel is centrally cut out of said elongated cylinder-shaped body.

6. The device of claim 1, wherein said handle has an opening for receiving said guiding sleeve, an outer contour of said guiding sleeve being such that said guiding sleeve can be only pushed into said opening in said handle in certain alignments.

7. The device of claim 1, wherein an opening being provided at the distal end of said arm, an aiming wire pushed through said first guiding channel passes said opening.

8. The device of claim 7, wherein markings are provided at the distal end of said arm, adjacent to said opening in said arm, said markings representing target points for said further aiming wire which runs through the second guiding channel and through said at least one laterally open cannulation.

* * * * *